(12) United States Patent
Bix

(10) Patent No.: US 10,319,195 B1
(45) Date of Patent: Jun. 11, 2019

(54) SENSORY SLOT MACHINE

(71) Applicant: William T. Bix, Rensselaer, NY (US)

(72) Inventor: William T. Bix, Rensselaer, NY (US)

( * ) Notice: Subject to any disclaimer, the term of this patent is extended or adjusted under 35 U.S.C. 154(b) by 63 days.

(21) Appl. No.: 15/830,717

(22) Filed: Dec. 4, 2017

Related U.S. Application Data

(60) Provisional application No. 62/429,250, filed on Dec. 2, 2016.

(51) Int. Cl.
*A63J 5/02* (2006.01)
*G07F 17/32* (2006.01)
*G07F 17/34* (2006.01)
*A61L 9/00* (2006.01)

(52) U.S. Cl.
CPC ............... *G07F 17/34* (2013.01); *A61L 9/00* (2013.01); *A63J 5/025* (2013.01); *G07F 17/3209* (2013.01); *G07F 17/3211* (2013.01); *G07F 17/3216* (2013.01); *G07F 17/3246* (2013.01); *G07F 17/3251* (2013.01); *A61L 2209/11* (2013.01)

(58) Field of Classification Search
CPC .. G07F 17/34; G07F 17/3209; G07F 17/3211; G07F 17/3216; G07F 17/3246; G07F 17/3251; A61L 9/00; A63J 5/025
USPC .......................................................... 463/20
See application file for complete search history.

(56) References Cited

U.S. PATENT DOCUMENTS

| | | | |
|---|---|---|---|
| 6,530,842 B1 | 3/2003 | Wells et al. | |
| 8,308,562 B2 | 11/2012 | Patton | |
| 8,591,315 B2 * | 11/2013 | Gagner | G07F 17/32 463/20 |
| 8,740,690 B2 | 6/2014 | Arnone et al. | |
| 8,827,805 B1 * | 9/2014 | Caporusso | G07F 17/3227 463/25 |
| 8,888,550 B1 * | 11/2014 | Conner | A61L 9/145 446/15 |
| 9,694,299 B1 * | 7/2017 | Kouso | A63H 33/28 |
| 10,058,780 B2 * | 8/2018 | Ono | A63F 13/214 |
| 2004/0064995 A1 * | 4/2004 | Gilmore | A01M 31/008 43/1 |
| 2004/0235570 A1 * | 11/2004 | Rothschild | G07F 17/32 463/46 |
| 2007/0218970 A1 | 9/2007 | Patel et al. | |
| 2008/0014835 A1 | 1/2008 | Weston et al. | |
| 2009/0137312 A1 | 5/2009 | Walker et al. | |
| 2010/0016052 A1 * | 1/2010 | Gagner | G07F 17/32 463/16 |
| 2012/0231886 A1 * | 9/2012 | Gomez | G07F 17/32 463/32 |
| 2013/0072292 A1 | 3/2013 | Sutton et al. | |
| 2013/0274007 A1 | 10/2013 | Hilbert et al. | |

(Continued)

*Primary Examiner* — Jay Trent Liddle
*Assistant Examiner* — Ryan Hsu
(74) *Attorney, Agent, or Firm* — Cramer Patent & Design, PLLC; Aaron R. Cramer

(57) ABSTRACT

An olfactory and tactile interactive slot machine having a traditional slot machine enclosure with enhanced functions such as discharging a scent, producing wind, providing a stream of bubbles, and providing ground level fog, all based upon a game progression. The discharge of odors and other tactile effects is correlated to the occurrence of a specific displayed slot machine events. The apparatus provides a plurality of lights and speakers which also provide performance related feedback.

20 Claims, 2 Drawing Sheets

(56) References Cited

U.S. PATENT DOCUMENTS

| | | | |
|---|---|---|---|
| 2016/0059145 A1* | 3/2016 | Cortelyou | A63H 27/12 472/57 |
| 2017/0340764 A1* | 11/2017 | Wong | A61L 9/03 |
| 2018/0071627 A1* | 3/2018 | Ono | A63F 13/214 |

* cited by examiner

SENSORY SLOT MACHINE

RELATED APPLICATIONS

The present invention is a continuation-in-part of, was first described in and claims the benefit of U.S. Provisional Application No. 62/429,250 filed Dec. 2, 2016, the entire disclosures of which are incorporated herein by reference.

FIELD OF THE INVENTION

The present invention relates generally an olfactory and tactile interactive slot machine that provides performance-related feedback.

BACKGROUND OF THE INVENTION

Even those of us who don't gamble are drawn into the mystique of a slot machine. The flashing lights and loud sounds draw us in, while the pull handle and spinning wheels hold our attention. Then the sure knowledge that the next coin will be the big winner keeps us as a returning customer. The draw of the slot machine is incredible when one thinks that it is almost guaranteed to give you nothing when you place money in it. However, one (1) slot machine begins to look the rest after only a short while, and there is nothing to draw a potential gambler to one (1) machine or casino over the next. As such, casinos and slot machine manufacturers are on the continual lookout for new and exciting game themes and motifs. Accordingly, there exists a need for a means by which new and exciting slot machines can be introduced to the gambling public. The use of the slot machine provides players with a higher level of engagement when playing slot machines that is not only quick, easy, and effective, but addictive as well.

SUMMARY OF THE INVENTION

The inventor has recognized the aforementioned inherent problems and lack in the art and observed that there is a need for an olfactory and tactile interactive slot machine that provides performance-related feedback.

It is therefore an object of the invention to provide a slot machine, comprising an enclosure having an upper cabinet superjacent and contiguous with a lower cabinet and defining an enclosure interior, a controller which is disposed within the enclosure interior and in electrical communication with a power source and a central processing unit, a pull handle which is disposed upon an upper cabinet first side and in electrical communication with the controller and a console disposed upon a front face of the upper cabinet.

The console of the slot machine comprises a first video display in electrical communication with the controller, at least one (1) speaker in electrical communication with the controller, a card reader in electrical communication with the controller, at least one (1) scent generator in electrical communication with the controller and in fluid communication with a first material reservoir, at least one (1) bubble generator in electrical communication with the controller and in fluid communication with a second material reservoir, a coin dispenser in electrical communication with the controller, a payout receiver in electrical communication with the controller and in mechanical communication with a payout generator, a plurality of lights in electrical communication with the controller and a plurality of switches. In a separate embodiment the digital display may each comprise a touchscreen.

Insertion of a card within the card reader activates the slot machine if a specific threshold of credit exits within a digital account associated with the card. Upon activation of the slot machine, a user may engage in at least one (1) of a plurality of games of chance preprogrammed upon the central processing unit. The user may play at least one of the plurality of games by manipulation of at least one (1) switch or pull handle and view the game on the first video display. A payout event is triggered by a winning round of play. A light event is triggered by the winning round of play or a losing round of play. A sound event is triggered by the winning round of play or the losing round of play. A first visual event is displayed upon the first video display by the winning round of play or the losing round of play. An olfactory event is triggered by the scent generator by the winning round of play or the losing round of play. A bubble event is triggered by the bubble generator by the winning round of play or the losing round of play.

The lower cabinet may comprise a shelf. The lower cabinet may also comprise a fog generator which is in electrical communication with the controller and fluid communication with a third material reservoir. A fog event is triggered by the fog generator by the winning round of play or the losing round of play. The console may further comprise a wind generator. A wind event is triggered by the wind generator by the winning round of play or the losing round of play.

The upper cabinet may further comprise a winner light in electrical communication with the controller and which is larger than any of the plurality of lights. A winner light event is triggered by the winning round of play. The first material reservoir, the second material reservoir and the third material reservoir may be accessed by a door disposed within the upper cabinet.

The console may further comprise a second video display which is in electrical communication with the controller. A second visual event is displayed upon the second video display by the winning round of play or the losing round of play. The scent generator may comprise a scent grill which is disposed over the scent generator. The fog generator may comprise a fog grill disposed over the fog generator. The wind generator may comprise a wind grill disposed over the wind generator.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
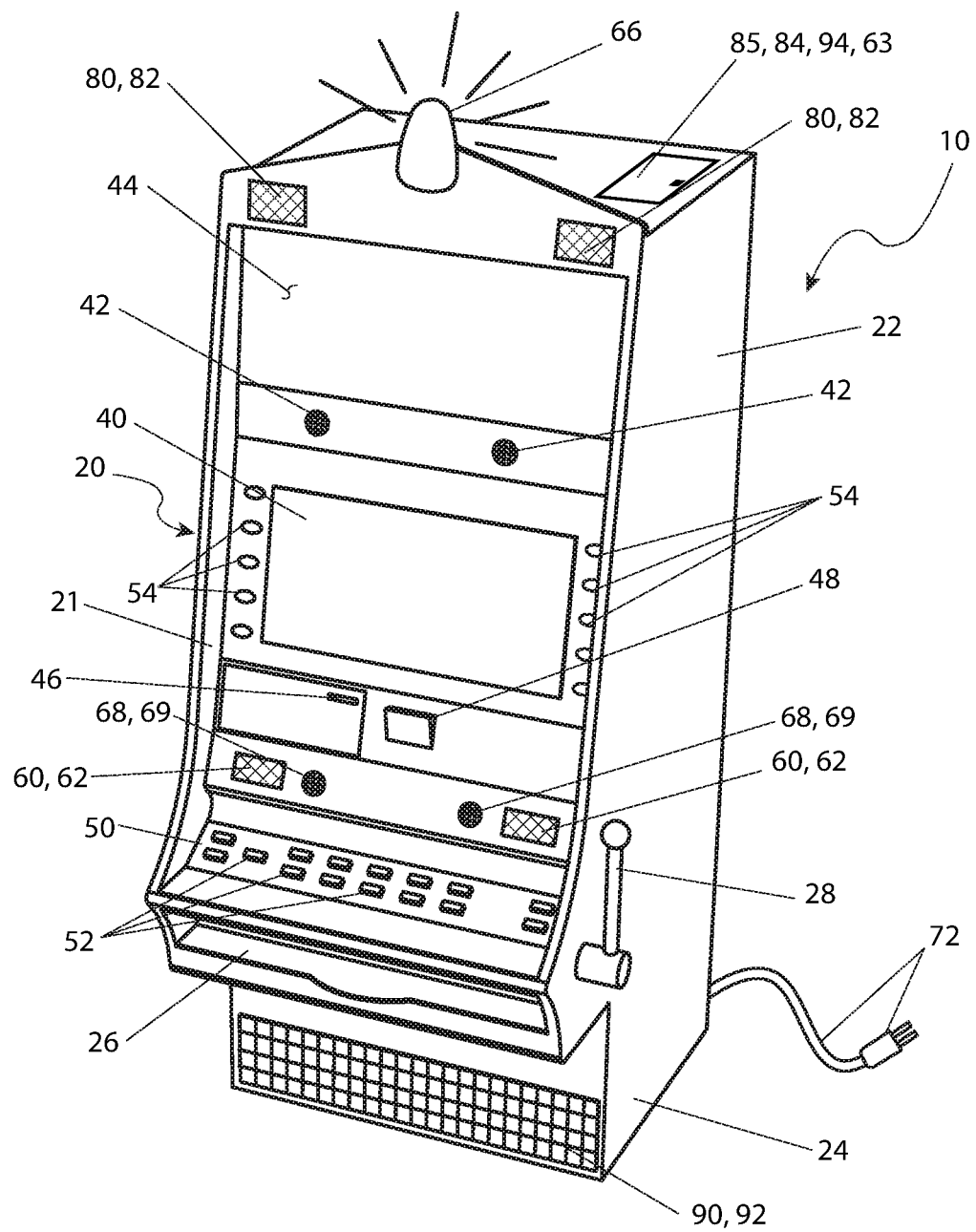
FIG. 1 is a front perspective view of an olfactory and tactile interactive slot machine 10, according to a preferred embodiment of the present invention; and, FIG. 2 is an electrical block diagram of the slot machine 10, according to a preferred embodiment of the present invention.

10 slot machine
20 enclosure
21 console
22 upper cabinet
24 base cabinet
26 shelf
28 pull handle 29 central processing unit
30 controller
32 wiring
40 first video display
42 speaker
44 second video display
46 credit card reader
47 coin/token dispenser
48 payout receiver
50 player interface console
52 selection buttons
54 row-lights
60 scent generator
62 scent grill
63 first material reservoir
64 scent motor/fan
66 "winner" light
68 wind fan
69 wind fan grill
72 power cord
80 bubble generator
82 bubble grill
84 second material reservoir
85 access door
86 bubble fan/motor
90 fog generator
92 fog grill
94 third material reservoir
96 fog fan/motor

DETAILED DESCRIPTION OF THE
PREFERRED EMBODIMENT

Figure 2:
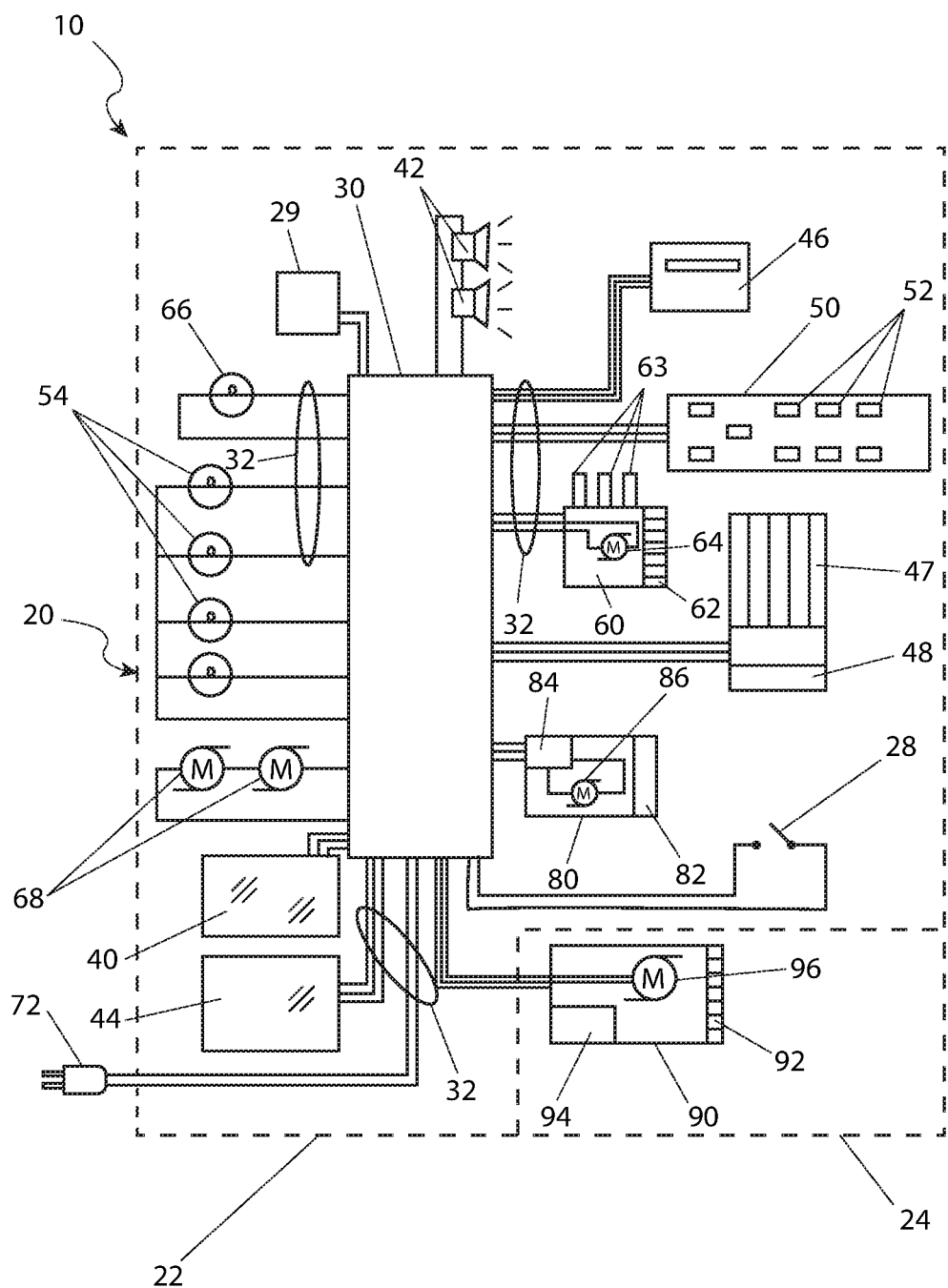

The best mode for carrying out the invention is presented in terms of its preferred embodiment, herein depicted within FIGS. 1 and 2. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope.

The terms "a" and "an" herein do not denote a limitation of quantity, but rather denote the presence of at least one (1) of the referenced items.

The present invention describes an olfactory and tactile interactive slot machine (herein described as the "apparatus") 10, which provides a slot machine with additional sensory features to enhance a slot machine playing experience such as, but not limited to: a scent generator 60, a wind fan 68, a bubble generator 80, and a fog generator 90.

Referring now to FIGS. 1 and 2, perspective and electrical block diagrams of the apparatus 10, according to a preferred embodiment of the present invention, are disclosed. The apparatus 10 provides equipment to release scents, produce fog, produce a stream of bubbles, simulate wind by blowing air, and provide sound and lighting effects depending upon the game progression. For example, during a game, visual graphics upon a display 40, 44 may depicting flight over an apple field and a subsequent scent of apples and a flow of air would be directed toward the player. The displays 40, 44 may also be touchscreen enabled thereby permitting the user to interact with the game.

The apparatus 10 includes an upright enclosure 20 including upper cabinet 22 and lower cabinet 24 sections. The upper cabinet 22 provides an attractive game displaying and operating means including a player interface console 50 similar to a conventional slot machine. In a preferred embodiment, the apparatus 10 further includes a shelf 26 for personal belongings, a large pull handle 28 to initiate a game sequence, a first video display 40, a second video display 44, two (2) audio speakers 42, a credit card reader 46, a coin/token dispenser 47, a bin-shaped payout receiver 48, a plurality of row-lights 54, and a top-mounted "winner" light 66. However, it is understood that the apparatus 10 is not limited to the particular number of and arrangement of the illustrated features described herein, and as such should not be interpreted as a limiting factor of the invention.

The upper cabinet portion 22 of the enclosure 20 further includes a scent generator 60 envisioned to evaporate and emit a perfumed flow of air towards the player as the progress of the game dictates. It is envisioned that a plurality of first material reservoirs 63 containing liquid scent would be evaporated via a scent fan/motor 64 which would in turn propel the scented air through a scent grill 62 toward the player. It is envisioned that scents such as food, flowers, perfume, or the like could be produced. Method of evaporation is well known in the art and is envisioned to include spontaneous evaporation in the open air, evaporation by application of heat directly to the vessel containing the liquid, evaporation by indirect application of heat from the fire, or evaporation under reduced pressure. The actual method of evaporation is not intended to be a limiting factor of the present invention.

The upper cabinet portion 22 also provides at least one (1) wind fan 68 which directs a flow of air through a wind fan grill 69 toward the player. Such wind effects could duplicate the effect of wind such as when riding a bicycle or when approaching a tornado or storm in conjunction with displayed graphics.

The upper cabinet portion 22 also provides a bubble generator 80 capable of propelling a flow of soap-based bubbles toward the player based upon the game progression. The bubble generator 80 is envisioned to employ a second material reservoir 84, and a bubble fan/motor 86 which generate the bubbles which are then emitted toward the player through at least one bubble grill 82 being positioned above the player (overhead level). An access door 85 on the top of the upper cabinet 22 provides access to refill or replace the second material reservoir 84 and the third material reservoir 94. The process of bubble generation by the bubble generator 80 is well-known in the art and could be accomplished by a multitude of methods such as rotating screen, air bubbler, or the like. The exact method of bubble generation is not intended to be a limiting factor of the present invention.

The base cabinet portion 24 of the enclosure 20 houses a fog generator 90 which emits a flow of fog from a fog grill 92 located in front of the player at ground level. The fog generator 90 is envisioned to employ a third material reservoir 94 and a fog fan/motor 96 portions to generate and propel the fog. The fog generator 90 is envisioned to utilize a liquid/steam/condensing unit, an inert gas, an electric pump to propel mineral oil, glycol, or glycerin and water mixture into a heat exchanger, where the solution is vaporized, or equivalent technology to generate the cloud-like fog effect. The exact method of fog generation employed by the fog generator 90 in the slot machine 10 is not intended to be a limiting factor of the present invention.

The apparatus 10 includes various electrical and electronic equipment within the enclosure 20 to control the aforementioned game enhancing systems via a controller 30. The exact nature of each game a user may play will vary depending upon the programming contained upon a central processing unit 29 which is in electrical communication with the controller 30. The central processing unit 29 is not limited to any particular game configuration and is envisioned to be of the sort including, but not limited to, those manufactured by Bally®, Williams®, and IGT®.

The controller 30 provides microprocessor-based circuit boards further including equipment such as, but not limited to: microprocessors, memory chips, embedded software, relays, and input and output signal management components. The controller 30 is in electrical and electronic communication via interconnecting wiring 32 with the first video display 40, the audio speakers 42, the second video display 44, a credit card reader 46, a coin/token dispenser 47, the player interface console 50, associated selection buttons 52, the scent generator 60, the "winner" light 66, the bubble generator 80, and the fog generator 90. The controller 30 receives and distributes electrical current throughout the apparatus 10 via a standard 110-volt power cord 72.

The sensory effects of the apparatus 10 are combined with the regular sight and sound effects of the slot machine to produce an enhanced experience leading to a higher level of excitement and fun, thus keeping the player at the slot machine even if not winning. The use of the apparatus 10 provides a player with a higher level of engagement when playing. However, if the person playing the slot machine 10 is sensitive or allergic to various scents, manipulation of the selection buttons 52, prior to play will provide the option to still play the slot machine 10, but not activate the scents during free play.

It is envisioned that other styles and configurations of the present invention can be easily incorporated into the teachings of the present invention, and only one (1) particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIG. 1.

The method of installing and utilizing the apparatus 10 may be achieved by performing the following steps: procuring a model of the apparatus 10 having desired software, hardware, and physical appearance; providing electrical power to the apparatus 10 by plugging the power cord 72 into an available 110-volt outlet; utilizing the credit card reader 46 to read a player's credit card and thereby fund and energize the gaming functions of the apparatus 10; utilizing the selection buttons 52 upon the player interface console 50 to select and configure game themes and to activate particular olfactory and tactile functions of the apparatus 10 as desired; initiating a game sequence by motioning the pull handle 28; enjoying the graphical displays upon the first 40 and second 44 video displays; experiencing the sensation of the olfactory and tactile functions of the apparatus 10 during play; continuing to initiate subsequent game sequences as desired; and, experiencing a winning sequence, thereby activating additional audio, visual, and tactile effects of the apparatus 10 as well as the "winner" light 66 and the dispensing of a payout into the payout receiver 48.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A slot machine, comprising:
an enclosure comprising an upper cabinet superjacent and contiguous with a lower cabinet and defining an enclosure interior;
a controller disposed within said enclosure interior and in electrical communication with a power source and a central processing unit;
a pull handle disposed upon an upper cabinet first side and in electrical communication with said controller;
a console disposed upon a front face of said upper cabinet comprising:
a first video display in electrical communication with said controller;
at least one speaker in electrical communication with said controller;
a card reader in electrical communication with said controller;
at least one scent generator in electrical communication with said controller and in fluid communication with a first material reservoir;
at least one bubble generator in electrical communication with said controller and in fluid communication with a second material reservoir;
a coin dispenser in electrical communication with said controller;
a payout receiver in electrical communication with said controller and in mechanical communication with a payout generator;
a plurality of lights in electrical communication with said controller; and,
a plurality of switches;
wherein insertion of a card within said card reader activates said slot machine if a specific threshold of credit exits within a digital account associated with said card;
wherein upon activation of said slot machine a user may engage in at least one of a plurality of games of chance preprogrammed upon said central processing unit;
wherein said user may play at least one of said plurality of games by manipulation of at least one said switch or said pull handle and view said one of said plurality of said games on said first video display;
wherein a payout event is triggered by a winning round of play;
wherein a light event is triggered by said winning round of play or a losing round of play;
wherein a sound event is triggered by said winning round of play or said losing round of play;
wherein a first visual event is displayed upon said first video display by said winning round of play or said losing round of play;
wherein an olfactory event is triggered by said scent generator by said winning round of play or said losing round of play; and,
wherein a bubble event is triggered by said bubble generator by said winning round of play or said losing round of play.

2. The slot machine of claim 1, wherein said lower cabinet comprises a shelf.

3. The slot machine of claim 2, wherein said lower cabinet comprises a fog generator in electrical communication with said controller and fluid communication with a third material reservoir;
  wherein a fog event is triggered by said fog generator by said winning round of play or said losing round of play.

4. The slot machine of claim 3, wherein said console further comprises a wind generator;
  wherein a wind event is triggered by said wind generator by said winning round of play or said losing round of play.

5. The slot machine of claim 4, wherein said upper cabinet further comprises a winner light in electrical communication with said controller and which is larger than any of said plurality of lights;
  wherein a winner light event is triggered by said winning round of play.

6. The slot machine of claim 1, wherein said first material reservoir, said second material reservoir and said third material reservoir are accessed by a door disposed within said upper cabinet.

7. The slot machine of claim 1, wherein said console further comprises a second video display in electrical communication with said controller;
  wherein a second visual event is displayed upon said second video display by said winning round of play or said losing round of play.

8. The slot machine of claim 1, wherein said scent generator comprises a scent grill disposed over said scent generator.

9. The slot machine of claim 8, wherein said fog generator comprises a fog grill disposed over said fog generator.

10. The slot machine of claim 9, wherein said wind generator comprises a wind grill disposed over said wind generator.

11. A slot machine, comprising:
  an enclosure comprising an upper cabinet superjacent and contiguous with a lower cabinet and defining an enclosure interior;
  a controller disposed within said enclosure interior and in electrical communication with a power source and a central processing unit;
  a pull handle disposed upon an upper cabinet first side and in electrical communication with said controller;
  a console disposed upon a front face of said upper cabinet comprising:
    a first video touchscreen display in electrical communication with said controller;
    at least one speaker in electrical communication with said controller;
    a card reader in electrical communication with said controller;
    at least one scent generator in electrical communication with said controller and in fluid communication with a first material reservoir;
    at least one bubble generator in electrical communication with said controller and in fluid communication with a second material reservoir;
    a coin dispenser in electrical communication with said controller;
    a payout receiver in electrical communication with said controller and in mechanical communication with a payout generator;
    a plurality of lights in electrical communication with said controller; and,
    a plurality of switches;
  wherein insertion of a card within said card reader activates said slot machine if a specific threshold of credit exits within a digital account associated with said card;
  wherein upon activation of said slot machine a user may engage in at least one of a plurality of games of chance preprogrammed upon said central processing unit;
  wherein said user may play at least one of said plurality of games by manipulation of at least one said switch, said pull handle, said first touchscreen video display and view said one of said plurality of said games on said first video display;
  wherein a payout event is triggered by a winning round of play;
  wherein a light event is triggered by said winning round of play or a losing round of play;
  wherein a sound event is triggered by said winning round of play or said losing round of play;
  wherein a first visual event is displayed upon said first video display by said winning round of play or said losing round of play;
  wherein an olfactory event is triggered by said scent generator by said winning round of play or said losing round of play; and,
  wherein a bubble event is triggered by said bubble generator by said winning round of play or said losing round of play.

12. The slot machine of claim 11, wherein said lower cabinet comprises a shelf.

13. The slot machine of claim 12, wherein said lower cabinet comprises a fog generator in electrical communication with said controller and fluid communication with a third material reservoir;
  wherein a fog event is triggered by said fog generator by said winning round of play or said losing round of play.

14. The slot machine of claim 13, wherein said console further comprises a wind generator;
  wherein a wind event is triggered by said wind generator by said winning round of play or said losing round of play.

15. The slot machine of claim 14, wherein said upper cabinet further comprises a winner light in electrical communication with said controller and which is larger than any of said plurality of lights;
  wherein a winner light event is triggered by said winning round of play.

16. The slot machine of claim 11, wherein said first material reservoir, said second material reservoir and said third material reservoir are accessed by a door disposed within said upper cabinet.

17. The slot machine of claim 11, wherein said console further comprises a second video touchscreen display in electrical communication with said controller;
  wherein a second visual event is displayed upon said second video touchscreen display by said winning round of play or said losing round of play.

18. The slot machine of claim 11, wherein said scent generator comprises a scent grill disposed over said scent generator.

19. The slot machine of claim 18, wherein said fog generator comprises a fog grill disposed over said fog generator.

20. The slot machine of claim 19, wherein said wind generator comprises a wind grill disposed over said wind generator.

* * * * *